United States Patent [19]

Culkin

[11] Patent Number: 4,602,989

[45] Date of Patent: Jul. 29, 1986

[54] METHOD AND APPARATUS FOR DETERMINING THE ZETA POTENTIAL OF COLLOIDAL PARTICLES

[75] Inventor: Joseph B. Culkin, Wilton, Conn.

[73] Assignee: Dorr-Oliver Incorporated, Stamford, Conn.

[21] Appl. No.: 776,737

[22] Filed: Sep. 17, 1985

[51] Int. Cl.⁴ ............................................. G01N 27/26
[52] U.S. Cl. ............................. 204/180.1; 204/183.1; 204/183.3; 204/186; 204/191; 204/299 R; 204/302; 204/305
[58] Field of Search ............... 204/180.1, 183.3, 183.1, 204/186, 191, 299 R, 302, 305

[56] References Cited

U.S. PATENT DOCUMENTS

| | | | |
|---|---|---|---|
| 3,320,148 | 5/1967 | Skeggs | 204/183.3 |
| 3,708,402 | 1/1973 | Bean | 204/183.3 |
| 3,909,380 | 9/1975 | Day et al. | 204/180.1 |
| 3,930,982 | 1/1976 | Batha | 204/186 |
| 3,941,678 | 3/1976 | Akiyama | 204/183.3 |
| 4,011,044 | 3/1977 | Uzgiris | 204/183.3 |
| 4,046,667 | 9/1977 | Goetz | 204/183.3 |
| 4,097,153 | 6/1978 | Deremigis | 204/180.1 |
| 4,113,596 | 9/1978 | Treille et al. | 204/180.1 |
| 4,242,194 | 12/1980 | Steiner et al. | 204/199 R |

*Primary Examiner*—Arthur P. Demers
*Attorney, Agent, or Firm*—P. D. Greeley; B. J. Kearns; G. R. Plotecher

[57] ABSTRACT

A method and apparatus for determining the zeta potential of particles in a suspension comprising: a cell containing at least a portion of the suspension of particles; a first electrode and a second electrode disposed in a cell; means for producing an electric field between the first and second electrodes, the electric field causing the particles to accelerate; means for converting a force, the force being generated by the acceleration of the particles, into electrical energy; and means for measuring the electrical energy.

46 Claims, 2 Drawing Figures

METHOD AND APPARATUS FOR DETERMINING THE ZETA POTENTIAL OF COLLOIDAL PARTICLES

BACKGROUND OF THE INVENTION

The present invention relates to a method and apparatus for determining the zeta potential of particles in a suspension comprising, a cell containing at least a portion of the suspension of particles; a first electrode and a second electrode disposed in the cell; means for producing an electric field between the first and second electrodes, the electric field causing the particles to accelerate; means for converting a force, the force being generated by the acceleration of the particles, into electrical energy; and means for measuring the electrical energy. In particular, the present invention provides a novel method and apparatus for determining the zeta potential of colloidal particles by means of measuring the force created when an unsteady driving voltage is applied to the electrodes of a cell, the mechanical force produced by acceleration of the particles is converted to an electrical energy or signal by a piezoelectric mechanical resonator and the electrical energy being detected by a synchronous demodulator.

Determination of the zeta potential of particles in a suspension is very helpful in controlling the addition of auxiliary agents to influence the flocculation and retention characteristics of particles. The addition of auxiliary agents can substantially influence the zeta potential and it is for this reason that much time has been devoted to methods and apparatuses to be used in determining the zeta potential of colloidal particles.

Many attempts have been made at measuring the zeta potential among them the use of ultrasonic sound to measure the vibration potential between two electrodes, and application of a laser beam for optical measurements thereof to determine the electrophoretic mobility of the migrating particles. The use of ultrasonic sound to measure the vibration potential of particles in suspension is disclosed in U.S. Pat. Nos. 4,294,656, 4,381,674 and 4,497,208.

U.S. Pat. No. 4,294,656 provides for a process for measuring zeta potential wherein a portion of the suspension is exposed to an ultrasonic field in a measuring cell, the measuring cell having two electrodes which extend into the suspension and are spaced from each other by an odd multiple of half ultrasonic wave length of the ultrasonic field in the suspension, and generating a signal from the voltage thereby formed between the electrodes which corresponds to the state of charge and determines the addition of auxiliary agent.

U.S. Pat. No. 4,381,674 discloses a method of detecting and identifying particulates in the recycling fluid flow of an oil recovery system by counting the number of ultrasonic pulses reflected from the particulates and comparing the number counted with the amount of ultrasonic energy across the flow.

U.S. Pat. No. 4,497,208 discloses a method and apparatus for measuring electro-kinetic properties of charged particles dispersed in a liquid medium which comprises the step of positioning two electrodes to contact the liquid medium, energizing the electrodes with an alternating electrical potential to cause a charged separation between the surfaces of the dispersed particles and the charged layers which surround the particles in the liquid medium and thereby to generate an acoustic signal, spacing an acoustic transducer from the electrodes for detecting an acoustic signal, and measuring the amplitude of the detected signal, the amplitude of the detected signal apparently being a function of the electro-kinetic properties of the particles present in the liquid medium, the number of particles per unit volume and the amplitude of the excitation potential on the electrodes.

Another means of measuring the zeta potential of colloidal particles is described in U.S. Pat. No. 4,046,667 which provides for a microelectrophoresis apparatus for measuring the zeta potential or electrophoretic mobility of particles suspended in a bulk medium, e.g. colloids suspended in a liquid. It further provides for the use of a light beam, microscope and objective lens system for physically determining the zeta potential of colloidal particles. The use of the microscope and light beam according to U.S. Pat. No. 4,046,667, however, requires a highly trained technician to physically determine the zeta potential. This system is inherently subject to human error and also requires prolonged analysis prior to each measurement.

The aforementioned patents relate either to the measuring of a vibration potential by use of ultrasonic sound in a frequency range of above 100 khz or to the measurement of electrophoretic mobility by the use of optical methods. Ultrasonic methods which measure a so-called "vibration potential" suffer from a lack of adequate theory linking vibration potential measurements to familiar colloidal properties such as zeta potential. Optical methods suffer from complexity and human error in the measurement of electrophoretic mobility.

The present inventor proposes a novel means and apparatus which avoids the inaccuracies and disadvantages of the prior art. Moreover, the present invention provides a method and apparatus for detecting an electrical signal which is directly proportional to the zeta potential of colloidal particles. The present invention also overcomes the disadvantage of the prior art which requires periodic testing by trained technicians. The advantages of a method and apparatus according to the present invention will be further described below.

SUMMARY OF THE INVENTION

It is the primary object of the present invention to provide a method and apparatus for determining the zeta potential (electro-kinetic potential) of charged colloidal particles in a suspension. In particular, it is an object of the present invention to provide a method and apparatus for determining the zeta potential of particles in a suspension comprising: inserting at least a portion of a suspension of particles in a cell, the cell having a first electrode and a second electrode; connecting the first and second electrodes to a power source for generating an unsteady electric field; accelerating the particles by the unsteady electric field; converting the force generated by the acceleration of the particles to electrical energy; and measuring the electrical energy by a detector.

Moreover, it is an object of the present invention to provide an apparatus for determining the zeta potential comprising: a cell containing at least a portion of the suspension of particles; a first electrode and a second electrode disposed in the cell; means for producing an unsteady electric field between the first and second electrodes, the unsteady electric field causing particles to accelerate; means for converting a force, the force being generated by the acceleration of the particles, into electrical energy; and means for measuring electrical energy.

It is also an object of the present invention that the cell can be inserted directly into a container or feed stream of the suspension of particles to be measured. The cell having first and second electrodes at opposite ends thereof.

It is a further object of the present invention to provide a power oscillator as the means for producing an unsteady electric field between the first and second electrodes, this field causing the particles to accelerate which in turn produces the force. According to the present invention the force produced by the acceleration of the particles in the cell is converted into electrical energy by means of a mechanical resonator. The mechanical resonator operates at the same frequency as the driving voltage produced by the power oscillator and is a piezoelectric force transducer.

Furthermore, it is an object of the present invention that the electrical energy converted from the mechanical resonator is measured by a synchronous demodulator. It is preferable according to the present invention to insert a FET input operational amplifier between the mechanical resonator and the synchronous demodulator.

Additionally, it is an object of the present invention that the voltage applied to the first and second electrodes from the power oscillator has a frequency in the range between 0-50 khz.

The present invention may also include many additional features which shall be further described below.

DESCRIPTION OF THE PREFERRED EMBODIMENT

Figure 1:
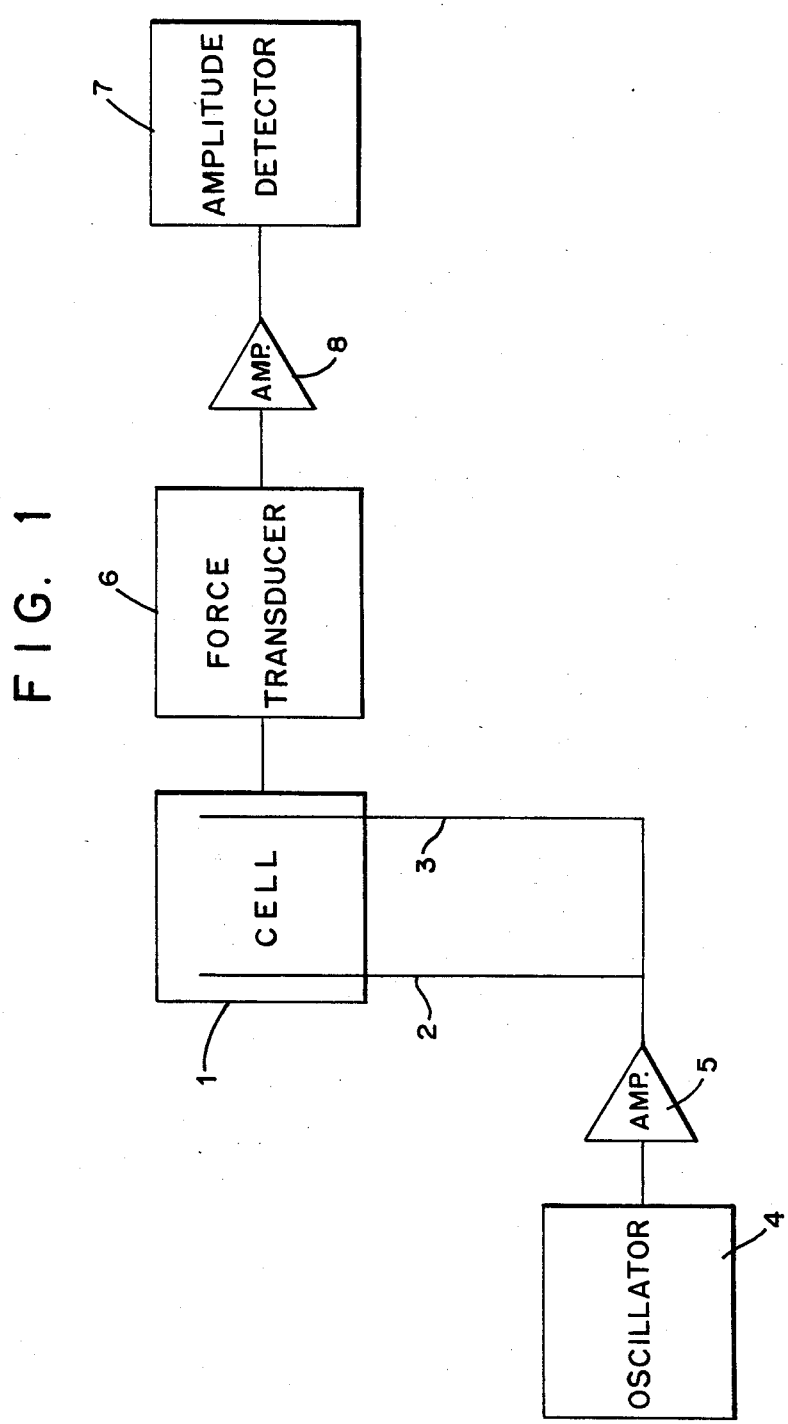
FIG. 1 is a block diagram detailing the present invention.

The present invention provides a novel method and apparatus which detects the unsteady force caused by the acceleration of the particles in suspension between a first and second electrode disposed within a cell. Accordingly, the unsteady force measured by the present invention is directly proportional to the zeta potential of the colloidal particles of suspension. The unsteady force can be easily detected (demodulated) using extremely accurate A-C signal detection techniques, e.g. synchronous demodulators. It has been found by the present inventor that it is important to limit the frequency of operation to a range between 0-50 khz, so that the unsteady acceleration of the cell will result in a rigid body translation of the entire cell contents. If frequencies in excess of 50 khz are attempted, the motion can no longer be described as a homogeneous acceleration of the liquid in the cell. Rather, the system must be described using an acoustic wave model similar to that used in measuring the so-called "vibration potential" which is treated in the prior art. This distinction, between a slowly accelerated cell undergoing a rigid body translational acceleration, and the acoustic wave system used by others serves to separate this invention from the prior art.

The zeta potential is particularly important when solids, such as kaolin clay particles, are placed into an electrolyte solution (sodium sulfate or other salts), a surface of the solids often become charged up relative to the bulk salt solution. Typically, this charging up of the solid surface is due to adsorption of one or several ions of a particular charge. Kaolin clay, for instance, tends to be an anion exchange material, that is, the clay particles tend to adsorb anions on its surface to neutralize immobile cationic exchange sites. The adsorption of anions on to the clay particles tend to make the particles become negatively charged. The charging of the small particles, i.e. less than 10 microns in diameter, is very important in determining the macroscopic behavior of a slurry of such particles. Such slurries occur in a wide variety of systems including paints, pigments, coal slurries, pulp and paper manufacturer, and many others.

The region of liquid near a charged solid surface in contact with electrolytes is called a diffuse double layer. In this region, two counterposed effects are in balance. On the one hand, ions, for example, cations, want to move towards the solid surface to join the adsorbed anions and thus produce a neutral space-charge distribution. On the other hand, cations mutually repel one another, and spontaneous aggregation of cations in one region of space near the particle constitutes a concentration gradient which tends to be reduced by diffusion away from the solid surface. The equilibrium distribution of cations outside the region of adsorbed anions is the result of a superposition of all these effects. The potential distribution which exists inside the double layer is roughly exponential in shape.

Thus, when electric fields are applied to the charged bodies, forces act on the charged bodies. The relationship being:

$$F = Eq \tag{1}$$

where F is the force, E is the electric field strength and q is the charge.

A particle in an electrolyte within an applied electric field will result in having a force couple acting to move the minus charges attached to the particle in one direction, and there will be opposing forces acting to move the plus charged liquid surrounding the particle and double layer in the opposite direction. Thus, there is a net migration of particles in one direction and liquid in the opposite direction. This in effect causes the particle to accelerate.

To define the zeta potential of a colloidal particle in suspension one must first determine the distribution of charge near the particle by the following equations: (1) Poisson's equations which relates charge density to electric potential; (2) the Poisson-Boltzman's equation which balances the desire of cations to join with anions against diffusion forces which resist the aggregation of cations into one region of space; (3) Ohm's law which relates the electric field strength to the conductivity of the electrolyte; and (4) the momentum equation where F=ma as applied to the liquid surrounding the particle and applied to the particle itself. These equations determine how colloidal particles will react to the application of electric field, e.g. by passing currents through a slurry.

To solve the system of coupled partial differential equations, one must apply boundary conditions. Thus, equations 1 and 2 above require the specification of a potential some place near the solid surface. Equation 4 requires that a no-slip condition be applied at the "shear-plane", where the "liquid" outer region of the ion cloud surrounding a particle becomes "solid" in nature, and shear is no longer allowed. The potential is often specified at a location coincident with the place where the no-slip condition is imposed. This potential is then defined as zeta potential.

Zeta potential is used in practice as a measure of the amount of charge adsorbed on to the particles in a suspension. Consider the case where a suspension of colloidal particles is settling or sedimenting out under the action of gravity. In such a case, charged colloidal particles are seen to migrate with a constant velocity toward the bottom of the vessel which contains the slurry. This movement of charge associated with the migrating particles constitutes a small electric current which in turn produces a small electric field. This electric field can be detected by inserting two electrodes spaced along the direction of migration of the particles. The potential detected by the electrodes is called the sedimentation potential. ($E_{sed}$)

$$E_{sed} = \frac{\epsilon Z}{3\mu\lambda} R^3(\rho_p - \rho_e)cg \quad (2)$$

where
$\epsilon = \epsilon_o D$
$\epsilon_o$ = permittivity of free space
D = dielectric constant of liquid
$\mu$ = fluid viscosity
$\lambda$ = fluid conductivity
R = particle radius
$\rho_p$ = particle density
$\rho_e$ = liquid density
C = particles concentration - #particles/unit volume
g = acceleration due to gravity
Z = zeta potential
$E_{sed}$ = sedimentation The steady acceleration of gravity produces a steady sedimentation potential which is extremely hard to detect because other steady potentials also exist due to non-sedimentation related effects. To make the sedimentation potential more easily detected, the present invention applies an unsteady acceleration to the entire system by vibrating the entire cell at a convenient frequency, e.g. 1 khz. The theory for sedimentation potential is then modified by substituting g=A sin ωt in the equation for sedimentation potential. Where A is the amplitude of the externally applied unsteady acceleration, ω is the frequency of the unsteady acceleration, and t is time. Thus, $$E_{used} = \frac{\epsilon Z}{3\mu\lambda} R^3(\rho_p - \rho_e)C\, A \sin \omega t \quad (3)$$

where $E_{used}$ is the unsteady sedimentation potential.

Conversely, the present inventor has discovered that when an unsteady electric field is applied, the result is a corresponding acceleration of the entire slurry which can be detected by a force transducer. This force can be calculated from a knowledge of known physical constants and material properties of the system. Thus, the force (F) is proportion to:

$$F \propto \frac{(\rho_p - \rho_e)C_p Z}{\mu} A \sin \omega t \quad (4)$$

where A is applied electric field amplitude, and F is the measured unsteady force. By averaging, the unsteady force amplitude can be accurately determined, e.g. by means of synchronous demodulation of the force signal.

The mechanical force is thus converted to electrical energy by means of a force transducer 6, such as a piezoelectric mechanical resonator. The piezoelectric element being, for instance, a lead-zirconium-titanate supported by a brass disc. The output voltage from the force transducer will be proportional to the zeta potential. The output voltage is measured by a detector 7, which may be a synchronous demodulator. An amplifier such as a FET input operational amplifier may be inserted between force transducer 6 and detector 7 to enhance the detecting of the small forces and energy signals achieved from force transducer 6.

Figure 2:
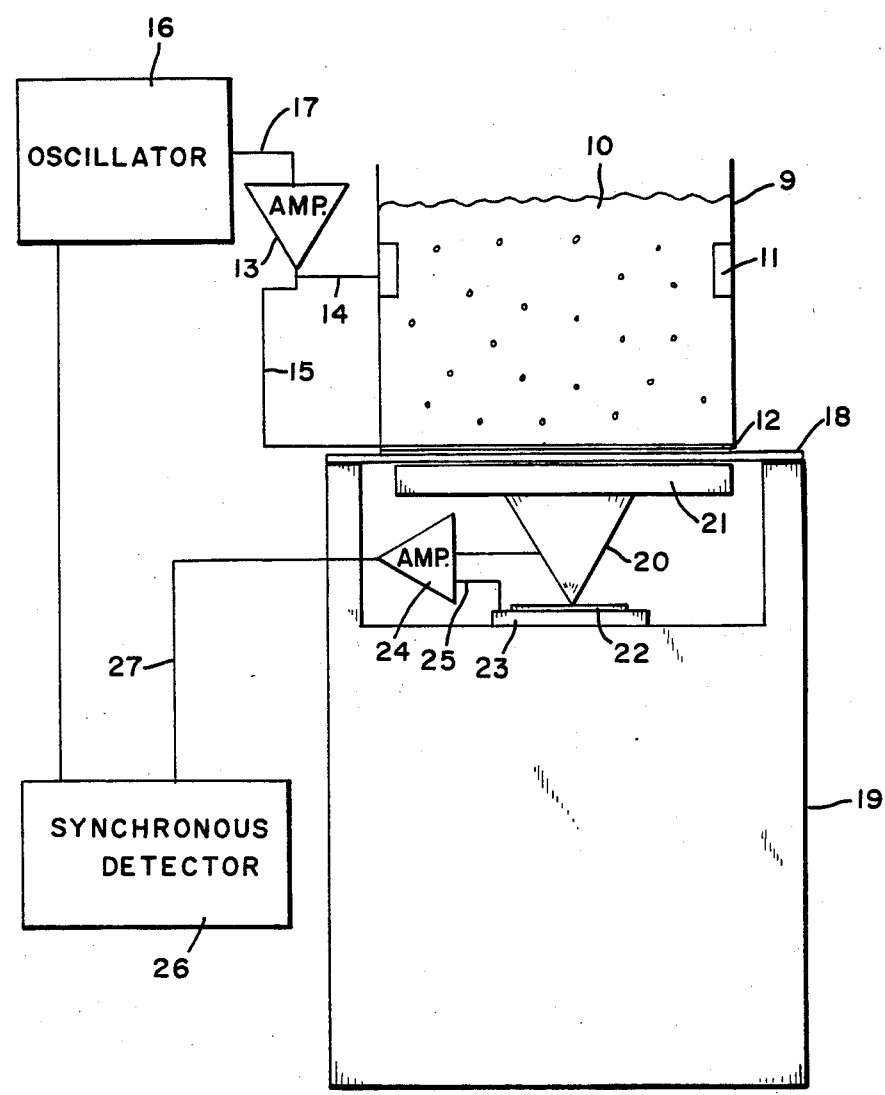
FIG. 2 is a sectional view of another embodiment according to the present invention.

FIG. 2 describes the preferred embodiment of the apparatus according to the present invention. Thus, FIG. 2 has a cell 9 containing particles in suspension 10 and electrodes 11 and 12 being disposed at opposite ends of cell 9. The electrodes 11 and 12 are made of electrically conductive material, such as platinum or stainless steel sheet metal. Electrode 11 is of a ring shape and adhered to the inner wall of cell 9 and electrode 12 is attached to cell 9 at one end thereof to seal one end of cell 9. Electrodes 11 and 12 are electrically connected to amplifier 13 via electrical wires 14 and 15, respectively. Amplifier 13 being electrically connected to a power oscillator 16 via wire 17.

Cell 9 is disposed on a plate 18, plate 18 being supported by stabilizing mass 19. On the opposite side of plate 18 from cell 9 is a cone 20 mounted on a base 21 and positioned such that the pinnacle of cone 20 is in contact with a force transducer 22. Force transducer 22 being a mechanical resonator formed from a piezoelectric crystal, e.g., a lead-zirconium-titanate piezoelectric crystal. A conductive disc 23 supports the force transducer 22 and transfers the electric signal which is converted by force transducer 22 from mechanical energy generated by the vibration of cell 9. The vibration of cell 9 being caused by the acceleration of particles 10 due to an electric field caused when a voltage is displaced across electrodes 11 and 12 via power oscillator 16. Disc 23 may be brass or the like and is electrically connected to an amplifier 24 via wire 25. Amplifier 24 may be a FET input operational amplifier which enhances the electrical signal received from the force transducer 22 which is thereafter detected by a synchronous demodulator 26 via wire 27.

Thus, the present invention operates such that either a portion of particles in suspension may be inserted into cell 9 or cell 9 may itself be inserted directly into a container or feed stream of particles in suspension for testing thereof. After cell 9 has been filled such that both electrodes 11 and 12 are simultaneously submerged in a suspension of particle 10, cell 9 is induced to vibrate by the application of an unsteady electric field caused by the application of an unsteady driving voltage of a frequency range between 0–50 khz generated from oscillator 16 and amplifier 13. The unsteady driving voltage according to the present invention between the first and second electrodes is approximately 10 to 100 volts.

An unsteady electric field being applied across electrodes 11 and 12 accelerates particles 10 in suspension thus resulting in vibration of cell 9. The vibration (Force) of cell 9 is coupled or transferred to a force transducer, such as a piezoelectric mechanical resonator 22, which is to operate at the same frequency as the unsteady driving voltage. The mechanical resonator 22 contains a piezoelectric force transducer which extracts mechanical energy, i.e. vibration of cell 9 caused by acceleration of particles 10 in the electric field, and converts the mechanical energy to an electrical signal. The electrical signal is then amplified via amplifier 24 and detected by a synchronous demodulator 26. Stabilizing solid 19 may be made of aluminum or the such and is of such a mass as to permit up to 70% conversion of mechanical energy into electrical energy.

Amplifier 24 is usually a FET input operational amplifier which is capable of providing extremely high power amplification. The electrical signal power available from the system as mechanical energy is $10^{-6}$ watts to $10^{-12}$ watts, depending on the contents of cell 9.

What is claimed is:

1. A method for determining the zeta potential of particles in a suspension comprising:
   inserting at least a portion of said suspension of particles into a cell, said cell having a first electrode and a second electrode;
   connecting said first and second electrodes to a power source for generating an electric field;
   accelerating said particles by said electric field;
   converting the force generated by the acceleration of said particles to electrical energy; and
   measuring said electrical energy by a detector.

2. The method according to claim 1, wherein said cell is inserted directly into a container or feed stream of said suspension of particles.

3. The method according to claim 1, wherein said first and second electrodes are positioned at opposite ends of said cell.

4. The method according to claim 1, wherein said electric field is generated by an unsteady driving voltage being applied to said first and second electrodes.

5. The method according to claim 4, wherein said unsteady driving voltage is generated from a power oscillator.

6. The method according to claim 5, wherein said power oscillator applies an alternating voltage between said first and second electrodes of approximately 10 to 100 volts.

7. The method according to claim 6, wherein a power amplifier is disposed between said power oscillator and said electrodes.

8. The method according to claim 1, wherein said force generated by acceleration of said particles is transmitted to said cell.

9. The method according to claim 8, wherein said force is transferred from said cell to a mechanical resonator which converts said force to electrical energy.

10. The method according to claim 8, wherein said mechanical resonator is tuned to resonate at the same frequency as the unsteady driving voltage.

11. The method according to claim 9, wherein said mechanical resonator is a piezoelectric force transducer.

12. The method according to claim 11, wherein said piezoelectric force transducer consists essentially of lead-zirconium-titanate and an electrically conductive support disc.

13. The method according to claim 1, wherein said detector for measuring the amplitude of said electrical energy is a synchronous demodulator.

14. The method according to claim 13, wherein an amplifier is disposed between said synchronous demodulator and said means for converting the force to electrical energy.

15. The method according to claim 14, wherein said amplifier is a FET input operational amplifier.

16. The method according to claim 1, wherein said electrical energy converted from said force is in the range of $10^{-6}$ to $10^{-12}$ watts.

17. The method according to claim 13, wherein the output signal of said synchronous demodulator is directly proportional to the zeta potential of said particles in a suspension.

18. The method according to claim 5, wherein the voltage applied to said first and second electrodes from said power oscillator has a frequency in the range between 0-50 khz.

19. An apparatus for determining the zeta potential of particles in a suspension comprising:
   a cell containing at least a portion of said suspension of particles;
   a first electrode and a second electrode disposed in said cell;
   means for producing an electric field between said first and second electrodes, said electric field causing said particles to accelerate;
   means for converting a force, said force being generated by the acceleration of said particles, into electrical energy; and
   means for measuring said electrical energy.

20. The apparatus according to claim 19, wherein said cell is inserted directly into a container or feed stream of said suspension of particles.

21. The apparatus according to claim 19, wherein said first and second electrodes are positioned at opposite ends of said cells.

22. The apparatus according to claim 21, wherein said cell contains a portion of said suspension of particles in an amount sufficient to submerge both said first and second electrodes in said suspension of particles.

23. The apparatus according to claim 19, wherein said cell is a glass cylinder closed at one end and open at the other end.

24. The apparatus according to claim 23, wherein said cell is closed at one end by means of an electrically conductive plate.

25. The apparatus according to claim 24, wherein said electrically conductive plate is also said first electrode.

26. The apparatus according to claim 25, wherein said electrically conductive plate consists essentially of stainless steel.

27. The apparatus according to claim 25, wherein said second electrode is positioned near said open end of said cell.

28. The apparatus according to claim 27, wherein said second electrode is an electrically conductive ring attached to the inner wall of said cell in contact with said suspension of particles.

29. The apparatus according to claim 28, wherein said ring consists essentially of stainless steel.

30. The apparatus according to claim 19, wherein said means for producing an electric field is said first and second electrodes electrically connected to a power oscillator.

31. The apparatus according to claim 30, wherein said power oscillator applies an unsteady driving voltage to said first and second electrodes.

32. The apparatus according to claim 31, wherein said power oscillator applies an alternating voltage between said first and second electrodes of approximately 10 to 100 volts.

33. The apparatus according to claim 30, wherein a power amplifier is disposed between said power oscillator and said first and second electrodes.

34. The apparatus according to claim 19, wherein said force generated by acceleration of said particles is transmitted to said cell.

35. The apparatus according to claim 19, wherein said means for converting said force into electrical energy is a mechanical resonator.

36. The apparatus according to claim 35, wherein said mechanical resonator is a piezoelectric force transducer.

37. The apparatus according to claim 36, wherein said piezoelectric force transducer consists essentially of lead-zirconium-titanate and an electrically conductive support disc.

38. The apparatus according to claim 35, wherein said mechanical resonator is disposed on a solid mass.

39. The apparatus according to claim 35, wherein said force is transferred to said mechanical resonator via an electrically conductive cone, said cone disposed such that the pinnacle of said cone is in contact with said mechanical resonator and the base of said cone is in insulated contact with said cell.

40. The apparatus according to claim 19, wherein said means for detecting said electrical energy is a synchronous demodulator.

41. The apparatus according to claim 40, wherein said synchronous demodulator is connected to said means for converting said force to electrical energy.

42. The apparatus according to claim 41, wherein an amplifier is disposed between said synchronous demodulator and said means for converting said force to electrical energy.

43. The apparatus according to claim 42, wherein said amplifier is a FET input operational amplifier.

44. The apparatus according to claim 19, wherein said electrical energy converted from said force is in the range of $10^{-6}$ to $10^{-12}$ watts.

45. The apparatus according to claim 40, wherein the output of the signal of said synchronous demodulator is directly proportional to the zeta potential of said particles in suspension.

46. The apparatus according to claim 30, wherein the voltage applied to said first and second electrodes from said power oscillator has a frequency in the range between 0–50 khz.

* * * * *